United States Patent [19]
Treptow et al.

[11] Patent Number: 5,844,686
[45] Date of Patent: Dec. 1, 1998

[54] SYSTEM FOR PIPETTING AND PHOTOMETRICALLY EVALUATING SAMPLES

[75] Inventors: Rainer Treptow, Norderstedt; Kurt Harnack, Tangstedt, both of Germany

[73] Assignee: Eppendorf-Netheler-Hinz, GmbH, Hauburg, Germany

[21] Appl. No.: 709,968

[22] Filed: Sep. 9, 1996

[30] Foreign Application Priority Data

Sep. 21, 1995 [DE] Germany ............... 195 35 046.4

[51] Int. Cl.⁶ ............................... G01N 21/01
[52] U.S. Cl. ................. 356/440; 356/246; 356/436
[58] Field of Search .................. 356/436, 440, 356/442, 246

[56] References Cited

U.S. PATENT DOCUMENTS

| | | | |
|---|---|---|---|
| 3,141,094 | 7/1964 | Strickler | 356/440 |
| 3,881,826 | 5/1975 | De Leeuw | 356/246 |
| 4,399,711 | 8/1983 | Klein | 356/341 |
| 4,420,254 | 12/1983 | Smeaton | 356/246 |
| 4,622,974 | 11/1986 | Coleman et al. | 356/246 |
| 4,933,291 | 6/1990 | Daiss et al. | 356/246 |
| 5,013,155 | 5/1991 | Rybak | 356/440 |
| 5,092,674 | 3/1992 | Garner | 356/440 |
| 5,125,748 | 6/1992 | Bjornson et al. | 346/414 |
| 5,171,537 | 12/1992 | Wainwright et al. | |
| 5,174,162 | 12/1992 | Miyake et al. | |
| 5,249,584 | 10/1993 | Karkar et al. | 356/246 |
| 5,402,241 | 3/1995 | Jeannotte et al. | 356/436 |
| 5,416,879 | 5/1995 | Liu | 356/440 |

FOREIGN PATENT DOCUMENTS

| | | |
|---|---|---|
| 391634 | 11/1990 | Austria . |
| 0038912 | 11/1981 | European Pat. Off. . |
| 0076406 | 4/1983 | European Pat. Off. . |
| 0332732 | 9/1989 | European Pat. Off. . |
| 0408181 | 1/1991 | European Pat. Off. . |
| 2040481 | 2/1972 | Germany . |
| 3046016 | 9/1981 | Germany . |
| 4222181 | 2/1993 | Germany . |
| 4342178 | 6/1995 | Germany . |
| 8700085 | 1/1987 | WIPO . |

*Primary Examiner*—Frank G. Font
*Assistant Examiner*—Zandra V. Smith
*Attorney, Agent, or Firm*—Anderson Kill & Olick, P.C.

[57] ABSTRACT

Hand apparatus for pipetting and photometrically evaluating samples which comprise a pipetting means, an integrated photometer and a replaceable pipette tip connected to said pipetting means, said pipette tip being defined as a cell and provided within the optical path of the photometer for photometrically evaluating absorbed samples.

35 Claims, 7 Drawing Sheets

SYSTEM FOR PIPETTING AND PHOTOMETRICALLY EVALUATING SAMPLES

BACKGROUND OF THE INVENTION

The invention relates to a system for pipetting and photometrically evaluating samples.

For analytics two tendencies are noticed: on the one hand, combining analytical facilities in large central labs, i.e. the places where to bring the substances and mixtures of substances to be analyzed. On the other hand, it is desirable to bring analytics and the substances to be analyzed into a closer contact with each other, i.e. to analyze the substance or the mixture where it is obtained.

For such "on-the-spot"-analytics any known photometrical facilities are not particularly suitable. The dosing of samples, mixing with reagents and photometrical evaluations up to now had only been possible with the aid of more or less large-scale equipments which do not allow a mobile use.

So from the DE 20 40 481 an apparatus for successive analyses of samples has become known, wherein a flow-through cell comprises a suction port and a piston-cylinder-unit. Lowering the flow-through cell into sample containers causes liquid to be drawn in through the passage of the measuring light of said flow-through cell and to be photometrically evaluated. On account of the necessary coordination of the evaluation with the lowering movement of the flow-through cell and the necessity of making available sample containers this apparatus involves quite some expense.

From the EP 0 332 732 A2 a device for carrying through photometrical and spectrophotometrical evaluations and chemical microreactions has become known. This device comprises a capillary tube to which a microcell is secured above including transparent walls for the use in a photometrical evaluating equipment. When used, the capillary is brought into contact with a small drop of blood. The blood is urged upwards by means of a plug provided within the capillary and centrifuged therein and is then forced from the capillary into the microcell with the aid of another plug material or any piston. There it can be mixed with a chemical reagent which is contained in a container the bottom of which may be opened within the microcell. This method makes an additional photometer necessary, is particularly intended for the analysis of blood and involves quite some expense.

From the EP 0 076 406 B1 an optical analytical method has become known which comprises providing a tube-shaped cell including a piston for taking in and delivering liquid through the extreme end of the same. The radiation from a radiation source is connected to the piston and is led through the latter and the absorbed liquid so that the optical way extends axially within the liquid from the piston to the open extreme end of the tube, in which case the absorbed liquid serves as a light guide. A sensor for the radiation leaving the tube is provided outside the cell. This apparatus involves quite some expense as well and makes a time-consuming handling necessary.

The AT 321 634B relates to an analyzer for analyzing the concentration and/or the activity of sample constituents of a liquid sample. The apparatus at least comprises a sensor being in contact with the sample, which sensor is incorporated into a pipette tip and with its active portion is immersed in the lumen of the pipette tip serving as evaluating chamber, into which a defined sample volume may be introduced by means of a pipetting key. The sensor may be arranged at the end of a fiber optics which is connected to a light source through an optocoupler and to a signal evaluation and display means in the pipette shaft through a beam splitter. The pipette tips comprising an optocoupler, integrated fiber optics and a sensor involve quite some expense and thus are not particularly suitable for single analyses. The purpose of the exchangeability of the pipette tips rather is to achieve an adaptation to the measuring situation by making use of different sensors.

Taking all this into consideration, it is the object of the invention to provide a system for pipetting and photometrically evaluating samples which is more suitable for those analyses, for which the pipette tips are used one time only and are thrown away then.

SUMMARY OF THE INVENTION

This problem is resolved by a hand apparatus characterized by the features of claim 1. Advantageous in which the pipette tip is defined as a cell and is provided within the optical path of the photometer for photometrically evaluating absorbed samples.

The inventive hand apparatus comprises a pipetting means including a pipette tip connected thereto which after pipetting of samples can be replaced by another pipette tip. In the hand apparatus the pipetting means is structurally combined with a photometer for photometrically evaluating any samples drawn into the pipette tip. The samples can be evaluated by the photometer outside or within the pipette tip. Advantageously, the pipette tip, for the first time, is defined as a cell and is provided within the optical path of the photometer when connected to the pipetting means. The pipette tip only serves the absorption of the liquid and as a cell then and may be defined as an inexpensive single-use tip which can be thrown away after use. The relatively expensive photometer, however, is entirely integrated into the pipetting means and, consequently, is used for all photometrical evaluations. This system allows samples and, possibly, reagents to be exactly dosed into quantities being suitable for the photometrical evaluation, to be mixed and, immediately thereafter, to be photometrically evaluated with the aid of the same means. By this, there, for the first time, a viable analytical "on-the-spot"-system for a wide field of applications, e.g. for hospitals, industry, ground/water, environment, biology and research, is made available.

Generally, there within the scope of the invention may be used any pipetting systems which control the absorption or release of liquid of a pipette tip connected thereto by appropriate measures. This may be a known pipetting means which, in most cases, is defined as a piston pipette. The piston pipette comprises a piston-cylinder-unit which upon activation draws a liquid into the pipette tip or releases the same. This unit may be provided within the pipetting means as well as within the pipette tip. Furthermore, the pipetting means with a controlling means may act upon a closed bubble-type displacement volume of a pipette tip in a known way so that liquid is transported through an opening of the tip. This version on account of the proximally closed pipette tip is particularly poor in contamination.

According to advantageous embodiments of the invention, it is provided that the pipetting means comprises an electric driving motor for a lifting piston as well as electronics, especially those including a display. The electronics may comprise a processor. Moreover, the electric drive may control a movement of the pipette tip for positioning, analyzing or mixing purposes or another mixing means. An accumulator is capable of supplying energy to all sinks, including photometer. The integrated photometer can comprise a miniature light source as spotlight (xenon or halogen) with fiber contact as well as a photodiode or diode row. Furthermore, a monochromator and a signal/noise suppression as well as a measuring amplifier can be provided.

The photometrical evaluation can comprise providing a full light transmission through the sample volume. However, there also can be evaluated optical constants of the sample (refractive index, absorption index) with the aid of a reflection element by using the ATR-technique (attenuated total reflection technique—compare Lexikon der Spektroskopie, edition 1993, author H. H. Perkampus, VCH-Verlag Weinheim). This can be defined as a semiconductor device including at least one light channel. It can be continuously connected to the photometer integrated into the pipetting means. However, it also can be connected to the pipette tip so as to define a single-use portion which, if made of plastics, also allows very low-priced cell-type pipette tips.

Preferably, microsystem technology or microoptics (reflection element in flip-chip technology) are used for the electronics or optics. A stabilized reagent or stabilized reagents for the samples to be analyzed can be made available in sealed pipette tips which, at the same time, serve as a cell. Any corresponding seals of the pipette tip are opened when used, e.g. by the pipetting means when making a connection to the pipette tip. Besides, the cell tips can be coded and the pipetting means can comprise a decoder. After taking up a pipette tip, e.g. from a thermally insulated container or another tip magazine, the pipetting means sees from the coding for which specific test the reagent is intended to be used. The pipetting means is then capable of automatically adjusting any test parameters, such as wavelengths, absorption volume, etc., by making use of stored data. A prompt facility can instruct the user by means of the display what to do next, e.g. the absorption of the liquid to be tested. Sample and reagent can be mixed in different ways, e.g. by up and down pumping of the liquid, the inner shape of the pipette tip or by the rotation thereof. The evaluation can be made automatically after sampling or mixture with the reagent.

For temperature-dependent kinetics of the reaction of sample and reagent a temperature control can be made by means of electrically or thermally conductive pipette tips or a mathematical compensation can be realized by temperature measurement. Besides, the test results can be stored.

The pipette tip can be put back into the tip magazine after use and be enclosed therein. It is thinkable to add the pipette tips to a disposal/supply circuit. The pipette tips usually are made of plastic material and intended for single use. The pipetting means can be kept in a pipette holder, a recharging of the accumulator being possible by means of a suitable means—e.g. inductively. In addition, the same or any other facilities can allow a data transmission between the pipetting means and the pipette holder. A bidirectional data traffic allows "transferring" the test results from the pipette to an electronic data processing via the pipette holder. In the other direction, an updating or completion of the methods and parameters is possible, as well as a list what "on-the-spot"-tests are still to be carried through.

Advantages of the invention, in particular, are seen in the combination of several process steps, the use of one apparatus only, the reduction of any mistakes possible, the reduced waste, the evaluation without any especially qualified personnel, the "off-the-line"-use, and the easy transportability of the system.

BRIEF DESCRIPTION OF THE DRAWINGS

Embodiments of the invention are shown in the drawings and are explained in more detail below. The figures show.

DETAILED DESCRIPTION OF THE PREFERRED EMBODIMENTS

Figures 1, 2:
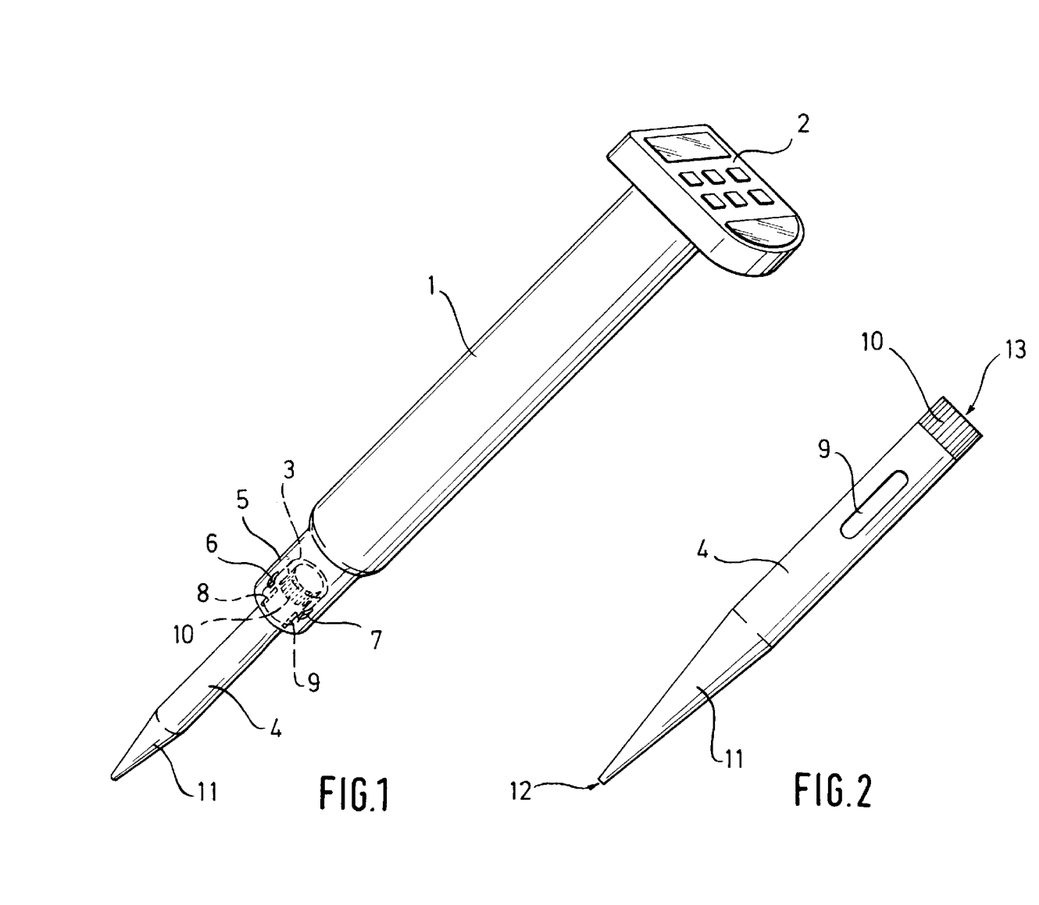
FIG. 1—a system comprising a pipetting means and a pipette tip, in a perspective side view.
FIG. 2—pipette tip of the same system, in front view.

According to FIG. 1, the system comprises a pipetting means defined as an electric piston pipette 1. The piston pipette 1 includes a head portion having a display and control panel 2. At the bottom it is provided with an accommodation 3 into which a pipette tip 4 is inserted and is retained therein. Insertion can be made in radial and/or in axial direction of the accommodation 3.

The piston pipette 1 comprises an integrated photometer which within the area of a surround 5 for the proximal end of the pipette tip 4 has an optical path which is characterized by diametrically opposite light outlet and inlet ports 6, 7.

The pipette tip 4 within the area of the optical path 6, 7 comprises two plane-parallel windows 8, 9 on opposite sides of its wall (compare FIG. 2). Furthermore, it includes a coding 10 at its proximal end which serves the transfer of information to an electronic evaluation means of the piston pipette 1. At its distal tip end the pipette tip 4 is tapered in a known way so as to form a cone 11. There an opening 12 of the tip for the liquid flow is provided while at the proximal end of the pipette tip 4 an opening 13 is provided for the air displaced by the piston.

Figure 3:
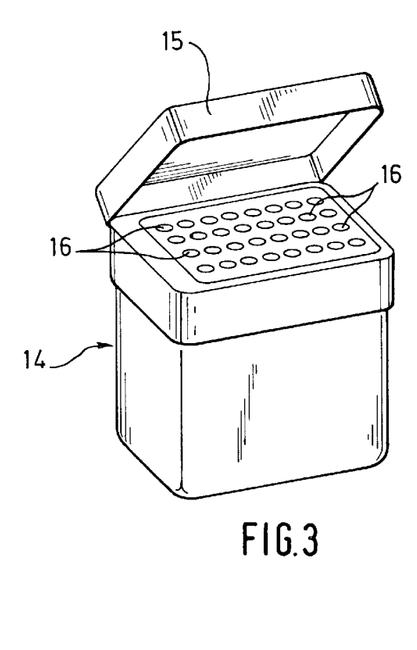
FIG. 3—tip magazine of the same system, in a perspective side view.

According to FIG. 3, pipette tips 4 are kept within a container 14 including a cover 15 which to provide a protection for reagents is heat-insulated. The pipette tips 4 are put into accommodation holes 16 in the upper area of the container 14 from which they can be removed by putting on the piston pipette 1 or can be replaced again in the reversed way.

Figure 4:
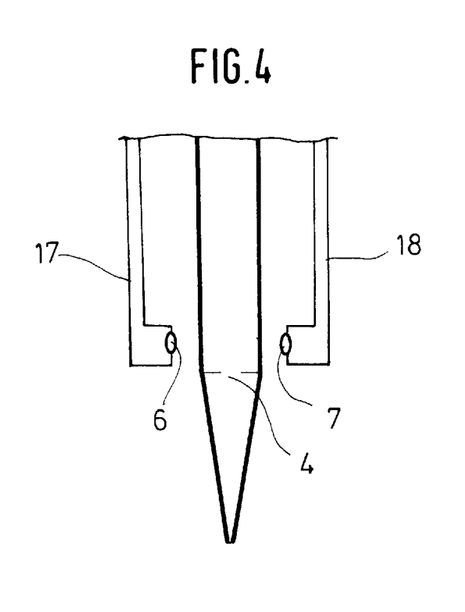
FIG. 4—photometer optics including the pipette tip of the system, in longitudinal section.

According to FIG. 4, light conducting fibers 17, 18 lead the light to the optical path 6, 7 or away from it. To eliminate environmental influences the light is modulated on the transmitter side 6 and demodulated by a pulsed rectifier on the receiver side 7.

Figure 5:
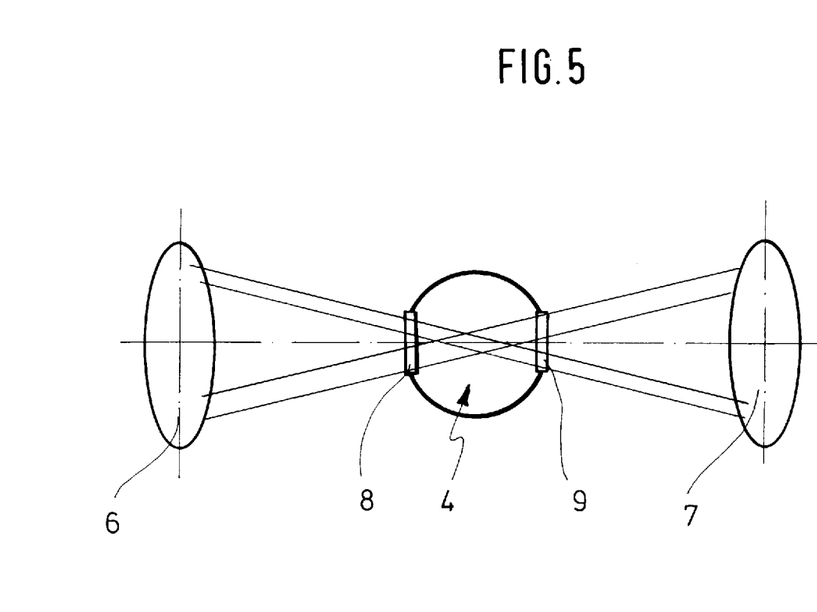
FIG. 5—transmission of radiation of the same optics, in an enlarged cross-section.

As can be seen from FIG. 5, the light at the end points of the optical path 6, 7 is focused by lenses so that the focal point for all wavelengths is directed to the sample volume of the pipette tip 4.

Figure 6:
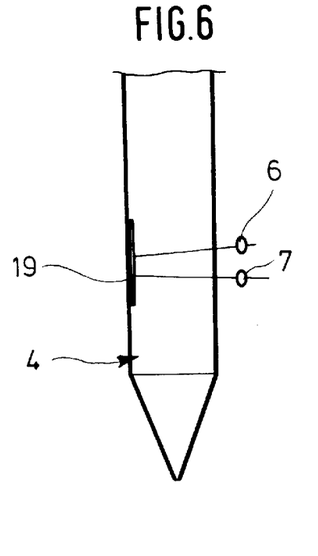
FIG. 6—transmission of radiation of another photometer optics with mirror-coated tip surface, in longitudinal section.
Figure 7:
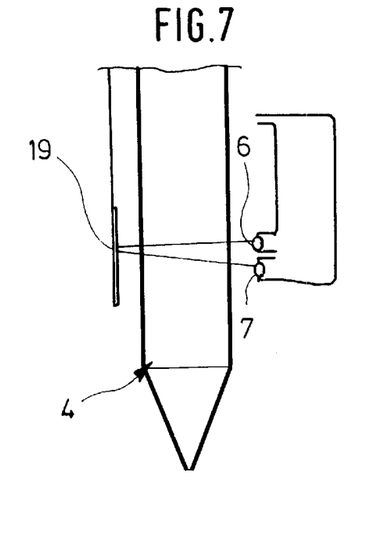
FIG. 7—transmission of radiation of another photometer-optics having a mirror surface with fixed pipette, in longitudinal section.

FIGS. 6 and 7 show a photometer including end points 6, 7 of the optical path on the same side of the pipette tip 4. The light rays are deviated by means of a mirror 19 which, according to FIG. 5, is arranged inside the pipette tip 4 and, according to FIG. 6, is provided outside the pipette tip 4.

Figure 8:
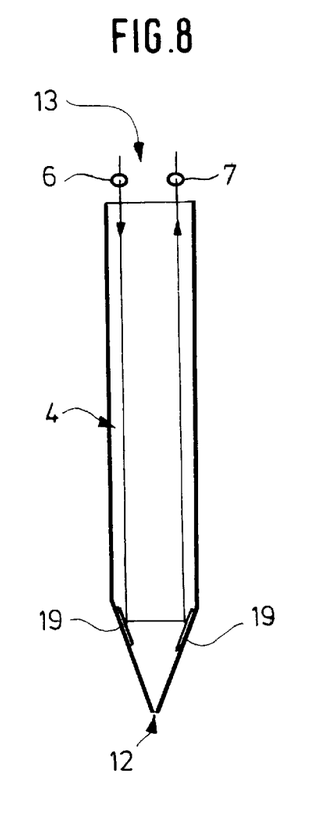
FIG. 8—transmission of radiation of another photometer optics with axial guidance of rays and mirror-coated tip surfaces, in longitudinal section.
Figures 9, 10:
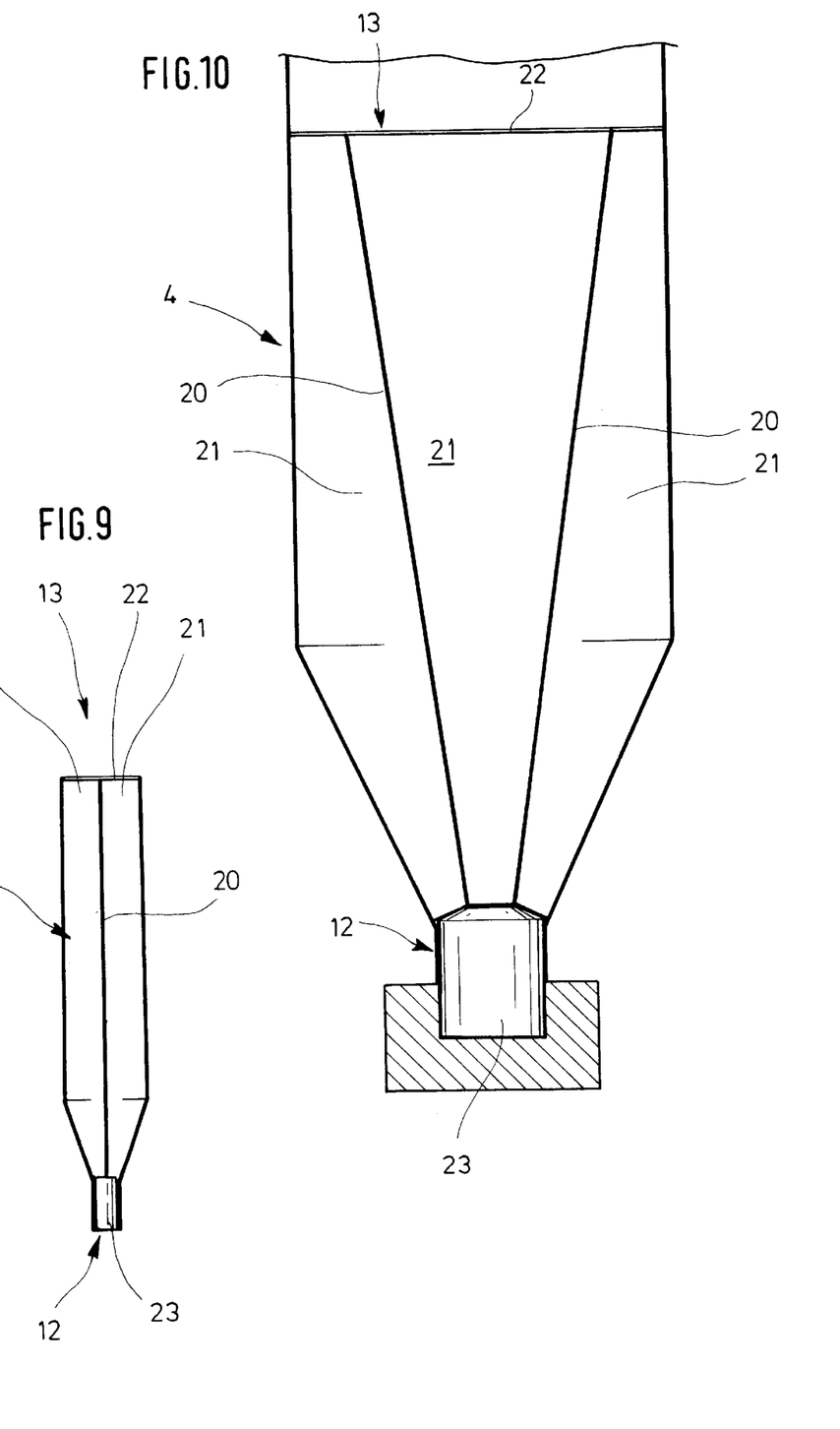
FIGS. 9 and 10—pipette tip comprising two or three chambers for different reagents, in longitudinal section.

According to FIG. 8, the optical path 6, 7 of the photometer can be directed axially through the proximal opening 13 into the pipette tip 4. Said pipette tip on its inner wall adjacent to the distal opening 12 includes mirror surfaces 19 for a deviation of the rays. FIGS. 9 and 10 show pipette tips 4 having parting walls 20 which before use separate reagents from each other in different chambers 21. The proximal opening 13 is closed by a seal 22 while the distal opening 12 is closed by a plug 23. When used, the seals 22, 23 are destroyed and the partitions removed so as to allow a reaction to take place prior to the photometrical evaluation.

Figures 11, 12:
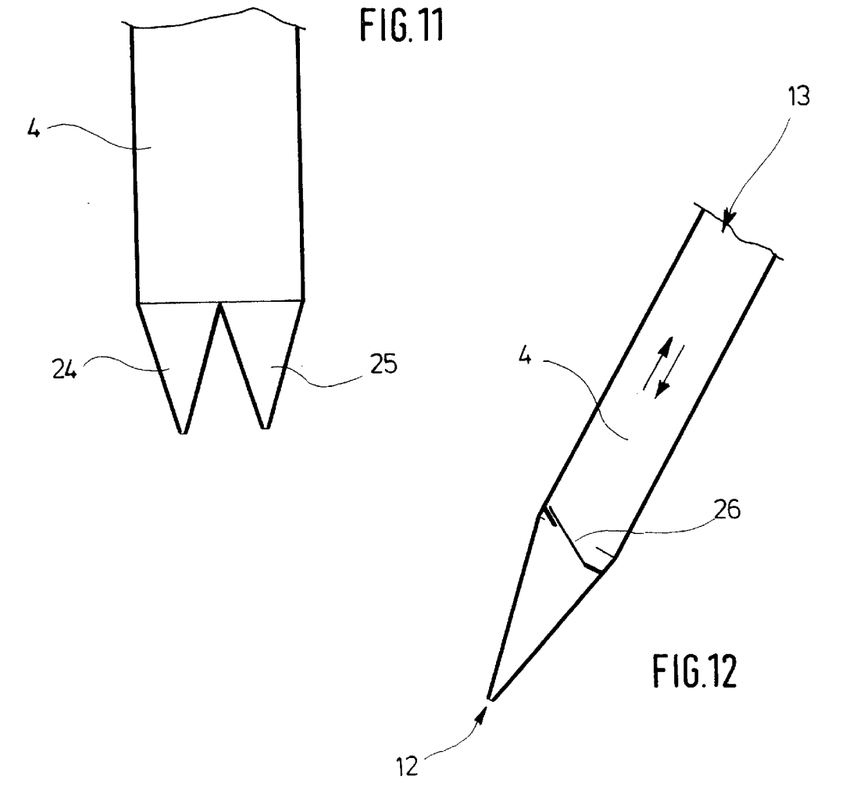
FIG. 11—pipette tip including two tip ends, in longitudinal section.
FIG. 12—pipette tip during mixing, in longitudinal section.

As can be seen from FIG. 11, a pipette tip 4 may comprise two conical tip ends 24, 25 which to avoid spreading effects serve the purpose of receiving the reagent and the sample.

According to FIG. 12, a pipette tip 4 adjacent to its distal opening 12 may comprise a shut-off mechanism 26 which allows liquid to only pass in the direction of the proximal opening 13 and prevents any spreading effects to be caused during the absorption of samples. This figure also shows that sample and reagent can be mixed within the pipette tip by up-and-down pumping in the direction of the shown arrows of motion. The mixing may be supported by suitable internal fittings or shaping of the inner cross-section (oval or rectangular) of the pipette tip 4. In particular, internal fittings and inner cross-section may also support a mixing by rotation of the pipette tip 4 with respect to the pipetting means.

Figure 13:
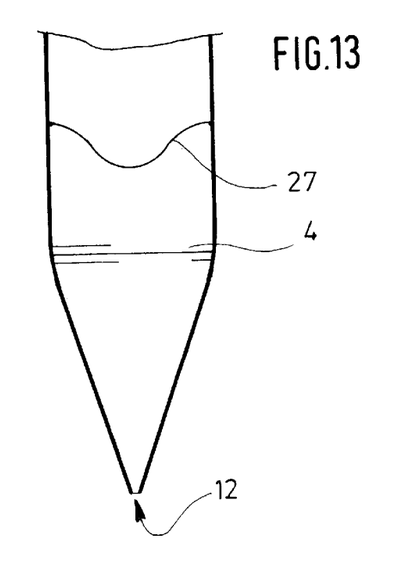
FIG. 13—pipette tip comprising a sealing membrane, in longitudinal section.

According to FIG. 13, the pipette tip 4 at its proximal opening may be closed by a membrane 27. The membrane 27 either is destroyed when using the pipette tip or serves the pressure transfer to the interior of the pipette tip for the purpose of delivering liquid through the distal opening 12 of the tip.

Figure 14:
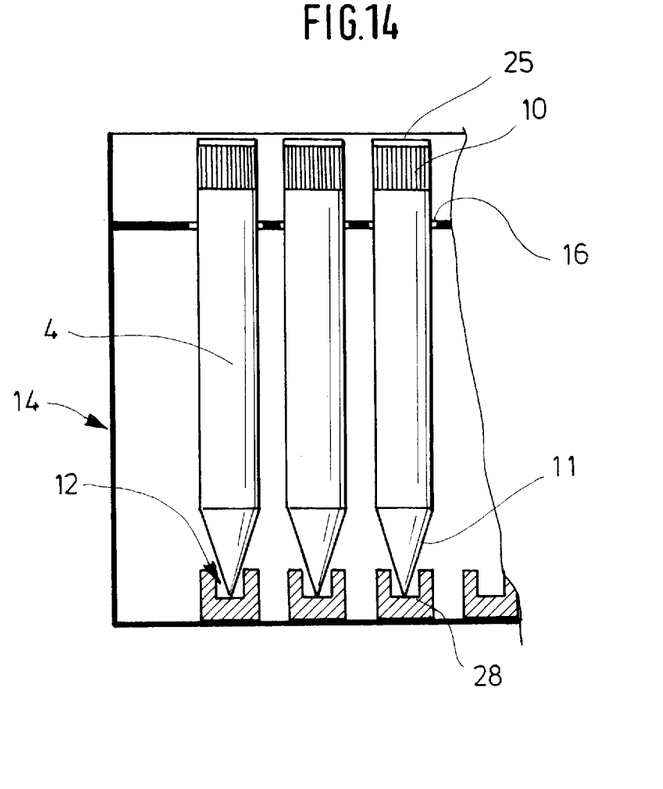
FIG. 14—pipette tip provided within the tip magazine, in a perspective side view.

According to FIG. 14, the pipette tips 4 kept within the container are closed by a fixedly located safety seal 28 provided at the bottom of said container. This safety seal is shaped like a cup which receives the cone end 11 of the pipette tip and seals the opening 12 of the tip defined therein. According to FIG. 12, the proximal end is sealed by means of a membrane 27. The pipette tip 4 with its coding 10 projects from the accommodation holes 16 so that a piston pipette can already identify the pipette tip when being put on by way of experiment.

Figure 15:
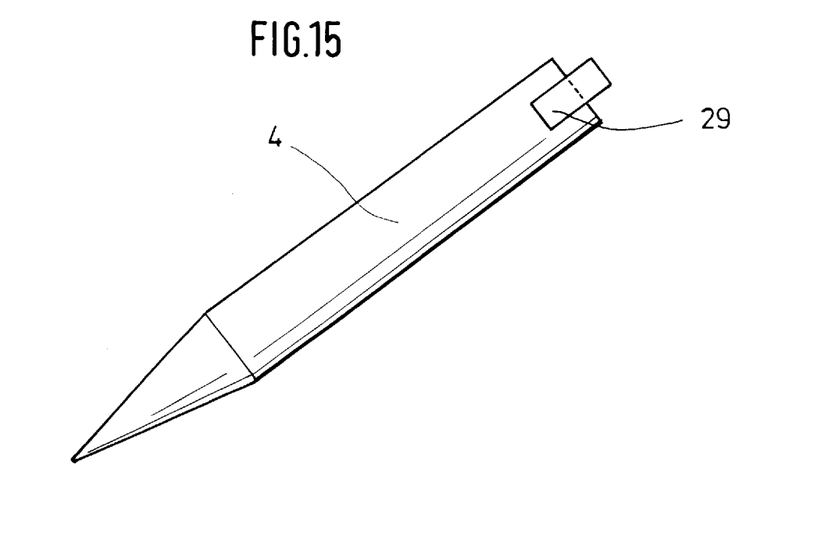
FIG. 15—pipette tip including a reflection element, in front view.
Figure 16:
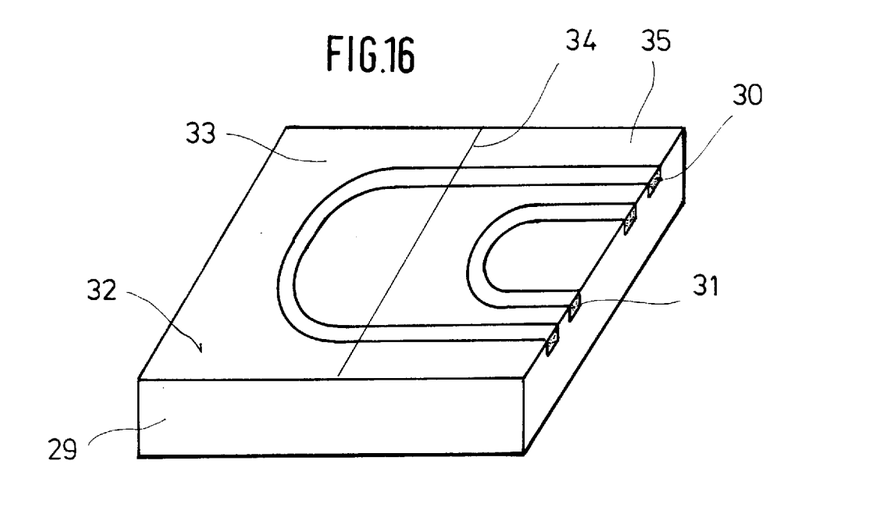
FIG. 16—reflection element in an enlarged lateral perspective view.
Figure 17:
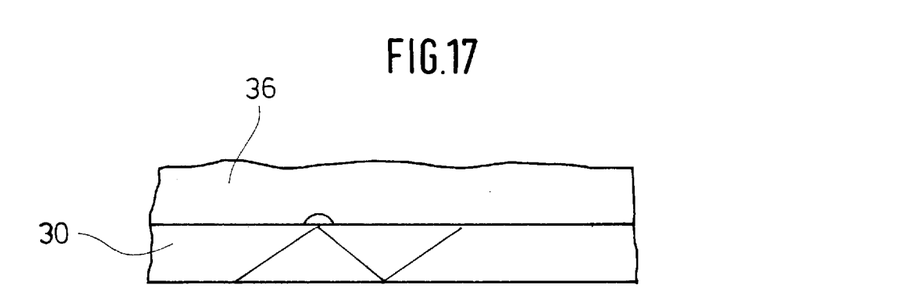
FIG. 17—measuring light channel of the reflection element, in an enlarged longitudinal section.

FIG. 15 shows a pipette tip 4 having a reflection element 29 for a photometer using ATR-technology, which reflection element is fixedly connected to the pipette tip. As appears from FIG. 16 more distinctly, the reflection element 29 is a plate-shaped semiconductor using flip-chip technology which comprises a horseshoe-shaped measuring light channel 30 and a reference light channel 31 also being horseshoe-shaped but smaller in size. The measuring light channel 30 and reference light channel 31 are provided adjacent to an inner surface 32 of the reflection element 29. The inner surface 32 with a measuring portion 33 (to the left of line 34 of the drawing) including the measuring light channel 30 is dipped into the sample volume of the pipette tip 4. The measuring surface 32 with its reference portion 35 (to the left of line 34 of the drawing) including the reference light channel 31 is provided outside the pipette tip 4. FIG. 17 shows that the optical path to a sample 36 dampening the measuring portion 33 is affected by the reflection within the fringe area. This affection allows the optical constant (refractive index and absorption index) of the sample volume 36 to be determined by means of the photometer.

For the photometrical evaluation the pipette tip 4 is connected to a piston pipette 1, with the reflection element 29 being connected to the optical path of the photometer.

Figure 18:
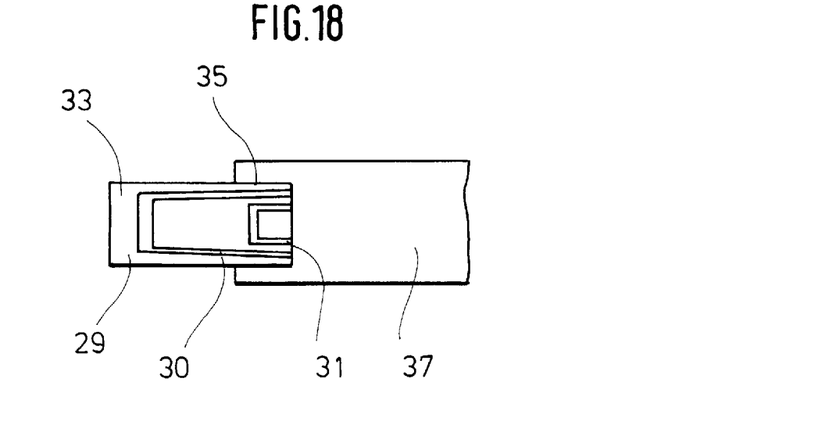
FIG. 18—photometer including reflection element, in front view.

FIG. 18 shows an alternative version, wherein a photometer 37—rough diagrammatic view—comprises a continuously connected reflection element 29. This, according to FIG. 16, is provided with a measuring light channel 30 and a reference light channel 31, in which case only the measuring portion 33 dips into a pipette tip 4 adapted to be slipped on.

We claim:

1. A hand apparatus for pipetting and photometrically evaluating samples which comprises a pipetting means, an integrated photometer and a replaceable pipette tip connected to said pipetting means, said pipette tip being defined as a cell and provided within the optical path of the photometer for photometrically evaluating absorbed samples.

2. The hand apparatus according to claim 1, wherein said pipetting means comprises at least one electric driving motor for transporting and/or mixing samples.

3. The hand apparatus according to claim 1, wherein said pipetting means comprises at least one electronic facility for evaluating measuring signals, entering, storing and displaying data and/or controlling device functions.

4. The hand apparatus according to claim 1, wherein said pipette tip includes a coding and said pipetting means comprises a decoder for reading said coding.

5. The hand apparatus to claim 1, wherein said pipetting means comprises an accumulator as electric power source.

6. The hand apparatus according to claim 1, wherein the optical path of the photometer is directed across the wall of the pipette tip.

7. The hand apparatus according to claim 1, wherein the optical path of the photometer is axially directed through a proximal opening of said pipette tip.

8. The hand apparatus according to claim 1, wherein said pipetting means and/or said pipette tip include mirrors for deviation of the optical path.

9. The hand apparatus according to claim 1, wherein said photometer measures reduction of light transmission by means of a sample volume.

10. The hand apparatus according to claim 1, wherein said photometer measures optical constants of a sample by means of a reflection element.

11. The hand apparatus according to claim 9, wherein said photometer comprises an optical reference path.

12. The hand apparatus according to claim 10, wherein said reflection element is a semiconductor plate including a measuring light channel and a reference light channel.

13. The hand apparatus according to claim 12, wherein said reflection element with said measuring light channel dips into the sample volume of said pipette tip and, together with said reference light channel, is arranged outside the sample volume of said pipette tip.

14. The hand apparatus according to claim 10, wherein said reflection element is fixedly connected to said photometer and is inserted into the sample volume of said pipette tip so as to be removable therefrom.

15. The hand apparatus according to claim 10, wherein said reflection element is fixedly connected to said pipette tip and is integrated into said optical path of said photometer so as to be detachable therefrom.

16. The hand apparatus according to claim 1, wherein said photometer comprises a modulator provided in front of a light transmitter, as well as a demodulator provided subsequent to a light receiver.

17. The hand apparatus according to claim 1, wherein said photometer includes light-conducting fibers for guiding light.

18. The hand apparatus according to claim 1, wherein said pipetting means receives a proximal end of said pipette tip in an accommodation and the optical path of said photometer is provided within an area of said accommodation.

19. The hand apparatus according to claim 1, wherein said pipette tip with at least one plane cell window is arranged within the optical path of said photometer.

20. The hand apparatus according to claim 1, wherein said pipette tip comprises at least one reagent.

21. The hand apparatus according to claim 20, wherein different reagents within said pipette tip are separated from one another by means of parting walls before making a connectiion to said pipetting means.

22. The hand apparatus according to claim 1, wherein said pipette tip is tightly sealed before connecting it to said pipetting means.

23. The hand apparatus according to claim 1, wherein said pipette tip includes a membrane-type outer wall.

24. The hand apparatus according to claim 1, wherein said pipette tip distally comprises a number of tip ends and tip openings for absorbing different liquids.

25. The hand apparatus according to claim 1, wherein said pipette tip includes an internal outline or internal fittings for speeding up mixing.

26. The hand apparatus according to claim 1, wherein said pipette tip comprises a valve element for allowing liquid to pass in one direction only.

27. The hand apparatus according to claim 1, wherein electronics and/or optics are using microsystem technology and/or microoptics.

28. An assembly comprising a hand apparatus for pipetting and photometrically evaluating samples which comprises a pipetting means, an integrating photometer and a replaceable pipette tip connected to said pipetting means, said pipette tip being defined as a cell and provided within the optical path of the photometer for photometrically evaluating absorbed samples; and a pipette holder for supporting the pipetting means.

29. The assembly according to claim 28, wherein said pipetting means comprises an accumulator as electric power source, and wherein said pipette holder and said pipetting means comprises facilities for charging the accumulator.

30. The means according to claim 28, wherein said pipette holder and said pipetting means comprise facilities for transmission of data.

31. The means according to claim 30, wherein said facilities for the transmission of data of said pipette holder are connected to an electronic data processing equipment.

32. The assembly according to claim 28, wherein a tip magazine is provided for keeping the pipette tip before or after making a connection to said pipetting means.

33. The means according to claim 32, wherein said tip magazine tightly seals inserted pipette tips by means of a closing element at least one opening.

34. The means according to claim 32, wherein said tip magazine is a container adapted to be closed.

35. The assembly according to claim 32, wherein said tip magazine is a heat-insulated container.

* * * * *

UNITED STATES PATENT AND TRADEMARK OFFICE
CERTIFICATE OF CORRECTION

PATENT NO.    : 5,844,686

DATED         : December 1, 1998

INVENTOR(S)   : Rainer Treptow, et al

It is certified that error appears in the above-identified patent and that said Letters Patent is hereby corrected as shown below:

On the title page, item

[73]    Assignee:    Eppendorf-Netheler-Hinz GmbH, Hamburg, Germany Signed and Sealed this Thirtieth Day of March, 1999

Attest:

Q. TODD DICKINSON

*Attesting Officer*    *Acting Commissioner of Patents and Trademarks*